United States Patent
Schwan et al.

(10) Patent No.: US 10,421,042 B2
(45) Date of Patent: Sep. 24, 2019

(54) ULTRAFILTRATION UNIT FOR CONTINUOUS BUFFER OR MEDIUM EXCHANGE FROM A PROTEIN SOLUTION

(71) Applicant: BAYER AKTIENGESELLSCHAFT, Leverkusen (DE)

(72) Inventors: Peter Schwan, Leverkusen (DE); Lutz-Peter Lenz, Solingen (DE); Kerstin Baumarth, Wuppertal (DE); Martin Lobedann, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 342 days.

(21) Appl. No.: 15/119,126

(22) PCT Filed: Feb. 13, 2015

(86) PCT No.: PCT/EP2015/053060
§ 371 (c)(1),
(2) Date: Aug. 15, 2016

(87) PCT Pub. No.: WO2015/121403
PCT Pub. Date: Aug. 20, 2015

(65) Prior Publication Data
US 2017/0056825 A1    Mar. 2, 2017

(30) Foreign Application Priority Data
Feb. 17, 2014 (EP) .................... 14155338

(51) Int. Cl.
*B01D 37/00* (2006.01)
*B01D 61/14* (2006.01)
(Continued)

(52) U.S. Cl.
CPC ......... *B01D 61/145* (2013.01); *B01D 61/243* (2013.01); *B01D 61/246* (2013.01);
(Continued)

(58) Field of Classification Search
None
See application file for complete search history.

(56) References Cited

U.S. PATENT DOCUMENTS 3,582,488 A    6/1971    Zeineh
4,670,152 A *  6/1987    Leonard .............. A61M 1/3643
                                                                210/137
(Continued)

FOREIGN PATENT DOCUMENTS

DE          4234728 A1     4/1994
DE    102007052571 A1     5/2009
(Continued)

OTHER PUBLICATIONS

Millipore, A Hands-On Guide to Ultrafiltration/Diafiltration Optimization using Pellicon® Cassettes, Printed in USA May 2013, pp. 1-12 (Year: 2013).*

(Continued)

*Primary Examiner* — Allison G Fitzsimmons
(74) *Attorney, Agent, or Firm* — McBee Moore Woodward & Vanik IP, LLC

(57) ABSTRACT

The invention relates to an ultrafiltration unit for continuous buffer or medium exchange, a method for continuous buffer or medium exchange in the ultrafiltration unit, and a plant in particular for (semi)continuous production of biopharmaceutical and biological macromolecular products in particular, such as proteins, e.g. monoclonal antibodies and vaccines, comprising the ultrafiltration unit according to the invention.

9 Claims, 3 Drawing Sheets

(51) Int. Cl.
    *B01D 61/24*     (2006.01)
    *B01D 61/28*     (2006.01)
    *B01D 61/32*     (2006.01)
    *B01D 61/58*     (2006.01)
    *B01D 63/02*     (2006.01)
    *C07K 16/06*     (2006.01)
    *C12M 1/00*     (2006.01)
    *C07K 1/34*     (2006.01)
    *C07K 16/00*     (2006.01)
    *B01D 61/00*     (2006.01)

(52) U.S. Cl.
    CPC ............ *B01D 61/28* (2013.01); *B01D 61/32* (2013.01); *B01D 61/58* (2013.01); *B01D 63/02* (2013.01); *C07K 1/34* (2013.01); *C07K 16/00* (2013.01); *C07K 16/065* (2013.01); *C12M 47/10* (2013.01); *B01D 2311/04* (2013.01); *B01D 2311/08* (2013.01); *B01D 2311/165* (2013.01); *B01D 2311/25* (2013.01); *B01D 2315/10* (2013.01); *B01D 2317/02* (2013.01); *B01D 2317/04* (2013.01)

(56) References Cited

U.S. PATENT DOCUMENTS 4,963,264 A     10/1990    Davis
5,702,606 A * 12/1997    Peter, Jr. .................... A61L 2/04
                                                       210/646
5,932,103 A *  8/1999    Kenley ...................... A61L 2/04
                                                       210/108
2004/0068219 A1    4/2004    Summerton et al.
2010/0307965 A1* 12/2010    Volker ................. B01D 61/025
                                                       210/232

FOREIGN PATENT DOCUMENTS

EP           0 911 042 A1    4/1999
EP           1 342 479 A1    9/2003
WO        2015007596 A1    1/2015

OTHER PUBLICATIONS

International Search Report of PCT/EP2015/053060 dated May 6, 2015.

Kurnik, Ronald et al., "Buffer Exchange Using Size Exclusion Chromatography, Countercurrent Dialysis, and Tangential Flow Filtration: Models, Development, and Industrial Application", Biotechnology and Bioengineering—Combinatorial Chemistry, Wiley, New York, NY, pp. 149-157, Jan. 1, 1995.

* cited by examiner

ULTRAFILTRATION UNIT FOR CONTINUOUS BUFFER OR MEDIUM EXCHANGE FROM A PROTEIN SOLUTION

CROSS-REFERENCE TO RELATED APPLICATIONS

This application is a National Stage entry of International Application No. PCT/EP2015/053060, filed Feb. 13, 2015, which claims priority to European Patent Application No. 14155338.8, filed Feb. 17, 2014. The disclosures of the priority applications are incorporated in their entirety herein by reference.

BACKGROUND

Field of the Invention

The invention relates to an ultrafiltration unit for continuous buffer or medium exchange, a method for continuous buffer or medium exchange in the ultrafiltration unit, and a plant in particular for (semi)continuous production of biopharmaceutical and biological macromolecular products in particular, such as proteins, e.g. monoclonal antibodies and vaccines, comprising the ultrafiltration unit according to the invention.

In the sense of the application, continuous operation means that the input of the feed stream into the bioreactor and the removal of the product stream from the production plant take place without a break, and many steps can be semi-continuous.

Description of Related Art

The strictly regulated production of pharmaceuticals requires a major time, technical and personnel effort for the preparation of purified and sterilized bioreactors and for ensuring a germ-free product. In order reliably to avoid cross-contamination in a product change in a multipurpose plant or between two product lots, apart from the cleaning, a very laborious cleaning validation is needed which must if necessary be repeated during process modification.

This applies both for upstream processing USP, i.e. the production of biological products in fermenters, and also for downstream processing DSP, i.e. the purification of the fermentation products.

It is precisely in fermentation that a germ-free environment is essential for successful culturing. For sterilization of batch or fed batch fermenters, the SIP technique (SIP=sterilization in place) is as a rule used. The reactor downtime due to the preparation procedures can be of the order of magnitude of the reactor availability, particularly in the case of short utilization periods and frequent product changes. In the USP, the biotechnological production, e.g. the process steps of medium preparation and fermentation, is affected, and in the DSP the solubilization, freezing, thawing, pH adjustment, product separation, for example by chromatography, precipitation or crystallization, buffer exchange and virus inactivation are affected.

In order to meet the requirement for rapid and flexible reloading of the production plant while maintaining maximal cleanliness and sterility, designs for continuous production, preferably with disposable technology, enjoy constantly growing interest on the market.

WO2012/078677 describes a method and a plant for continuous preparation of biopharmaceutical products by chromatography and integration thereof in a production plant, particularly in a disposable plant. Although WO2012/078677 provides approaches for continuous production of biopharmaceutical and biological products, the disclosed solution is in practice not sufficient.

A method for production of biopharmaceutical and biological products usually includes the following production steps, which are linked together:
1. Perfusion culturing
2. Cell retention system,
And, alternatively to steps 1 and 2, is a fed batch culture.
3. Cell separation
4. Buffer or medium exchange preferably with concentration
5. Bioburden reduction preferably by sterile filtration
6. Capture chromatography Normally further steps are performed for further purification of the product stream, in particular:
7. Virus inactivation
8. Neutralization
9. Optionally a further bioburden reduction (sterile filtration)

In view of the high quality standards in the production of biopharmaceuticals, these are normally also followed by the following steps:
10. Chromatographic intermediate and fine purification
11. Bioburden reduction e.g. sterile filtration
12. Virus filtration
13. Buffer exchange and preferably concentration
14. Sterile filtration.

In the production process described above, cells in a fermenter with nutrient solution produce a biological product. The nutrient solution is in this case also an ideal growth medium for microorganisms, such as bacteria and spores.

Hence one problem is to decrease the risk of microbial contamination in the subsequent process steps. The longer a process takes, particularly in a continuous process, the more vital it is to solve this problem. In the production of proteins, in at least one process step a buffer or medium exchange (=buffer exchange) of the product solution is performed.

Furthermore, sometimes laborious adjustments of one or more parameters of the feed stream/product stream, in particular concentration, volume/flow rate, pH and conductivity, are necessary for many process steps. In particular, various chromatographic steps can necessitate various fresh adjustments of one or more parameters of the feed stream. In addition, for a continuous process, a continuous process solution must preferably be found.

WO2012/078677 gives no details of a buffer or medium exchange or of the adjustment of the feed stream, particularly just before the chromatography unit, so that the applicability of the disclosed continuous plant is restricted to types of chromatography which require no particular adjustments, particularly as regards concentration, pH and conductivity.

In the state of the art, buffer exchange is known as a measure for adjusting the feed parameters in a batch process. Usually, a batchwise diafiltration with an ultrafiltration membrane is used. In this, a product solution is initially placed in a container. The solution is pumped in a circuit via an ultrafiltration membrane, wherein the product is as far as possible retained by the membrane, while salts/buffers are removed through the membrane as permeate. The fill level in the product container is usually kept constant since the permeate volume is replaced by washing fluid. The residual concentration of the salts in the product is then ideally calculated as follows:

C=Co*exp(wash volume/volume product solution), wherein Co is the initial concentration of the salt. This process is mostly incorrectly named as continuous diafiltration in the literature, although it is a batch process, since no feed stream is continuously fed into the container and no product stream is continuously removed from the container. This is due to the fact that buffer is continuously fed into the system until the batch is completely processed [Alois Jungbauer, "Continuous downstream processing of biopharmaceuticals", Trends in Biotech., 2013 (8), 479-492, WO2009017491].

Ultrafiltration modules are also used in haemodialysis, haemofiltration and haemodiafiltration. Haemodialysis differs from the other ultrafiltration methods in that it is a purely diffusive and not pressure-driven process. However, in terms of process technology, haemodialysis is also a batchwise process in which the human body can be regarded as the product container and the patient's blood must as a rule be washed over several hours. Moreover, in the state of the art, dialysis is known in the laboratory for desalting and buffer exchange of protein solutions. However because of the allegedly slow diffusion, dialysis is only a method for smaller laboratory volumes [ThermoScientific http://www.piercenet.com/browse.cfm?fld I D=5753AFD9-5056-8A 76-4E 13-5F9E9B4324DA, CN102703550].

Dynamic dialysis uses flow dynamics in order to increase both the rate and also the efficiency of the dialysis. By circulation of the sample and/or the dialysate, the highest possible concentration gradient is produced, in order considerably to shorten the dialysis time. Other advantages of the incident flow are that membrane soiling is prevented, while in many cases a pressure difference is created. This additional driving force increases the hypo-osmotic mass transfer rate across the semipermeable membrane and enables sample concentration during the dialysis procedure. Depending on the application, there are two basic methods, in which the dialysate streams and the sample can be either static or flowing. These methods are used for various reasons and for various purposes in dynamic dialysis. If the sample flows, in the state of the art it is conveyed in a circulation system including a product vessel [http://de.spectrumlabs.com/dialysis/Dynamic.html]. This method is also a batch method.

In the sense of the application, continuous diafiltration means that a feed stream and a wash stream are continuously fed into the ultrafiltration unit. In the sense of the application, semi-continuous operation means what in general is understood as lot or batch purification, i.e. that one or more lots of a protein solution from one or more containers are continuously fed into the ultrafiltration unit, wherein here the washing fluid is also continuously fed in.

An actual continuous diafiltration can be effected in the state of the art by connecting several diafiltration stages together in co-current flow or countercurrent flow. However, the equipment cost for this is correspondingly large [Alois Jungbauer, "Continuous downstream processing of biopharmaceuticals", Trends in Biotech., 2013 (8), 479-492].

No simple continuous solution for adjustment of the feed parameters and in particular for buffer exchange of the product stream is yet known.

U.S. Pat. No. 4,963,264 A discloses a dialysis unit and method which can be used for purification of antibodies. A hollow fibre module is used. Product and wash solution are fed in the countercurrent method, wherein the solutions are not circulated. By means of an affinity adsorbent, the target species is extracted to the other side of the membrane and thus is retrieved in the permeate. In a particular embodiment, U.S. Pat. No. 4,963,264 A states that for some experiments a counterpressure means was used in order to set up a variable pressure, without giving further details.

U.S. Pat. No. 3,582,488A discloses a unit and a method for dialysis, buffer exchange and/or concentration of biological species, e.g. of proteins. For this, a flat membrane module is used and the flows are conveyed in small channels which can also be regarded as capillaries. The unit is operated in the countercurrent method. As a pressure device in the outlet, U.S. Pat. No. 3,582,488A describes a clamp, in order to effect concentration of the product by creating a net flow, but not to effect improvement of buffer exchange.

KURNIK et al. discloses the buffer exchange of proteins by means of countercurrent dialysis using several hollow fibre membrane modules connected in series, without regulation of the outlet flow to control the net flow. A 100-fold enrichment can be achieved (KURNIK RONALD T ET AL: "Buffer exchange using size exclusion chromatography, countercurrent dialysis, and tangential flow filtration: Models, development, and industrial application", BIOTECHNOLOGY AND BIOENGINEERING—COMBINATORIAL CHEMISTRY, WILEY, NEW YORK, N.Y., US, Vol. 45, No. 2, 1 Jan. 1995 (1995 Jan. 1), pages 149-157, XP002311649).

SUMMARY

The first problem therefore consisted in the provision of a solution which enables adjustment of the product stream, in particular adjustment of the concentration, pH and/or conductivity of a continuous product stream, by buffer exchange. In particular, the solution should be flexible and enable the adjustment of the product stream to the requirements of one or more different chromatographic purification steps.

The problem was solved by the use of at least one hollow fibre ultrafiltration module (=capillary ultrafiltration module) operated in co-current, countercurrent or cross-current, preferably in countercurrent, preferably a haemodialysis module in an ultrafiltration unit, in which the product stream (=feed stream) and the washing fluid (=dialysate) are flowing, wherein the buffer exchange is effected without circulation of the product stream and the washing fluid in the hollow fibre ultrafiltration module.

In the application, the product stream which is conveyed into the capillary is as usual in membrane technology also called feed stream or feed. In the application, product stream which is conveyed out of the capillaries is as usual in membrane technology also called retentate.

In the application, the washing fluid which is conveyed into the capillary is as usual in membrane technology also called dialysate, dialysis buffer or permeate. The washing fluid which is conveyed out of the capillaries is also called waste stream in the application.

DETAILED DESCRIPTION OF A PREFERRED EMBODIMENT

Figure 1:
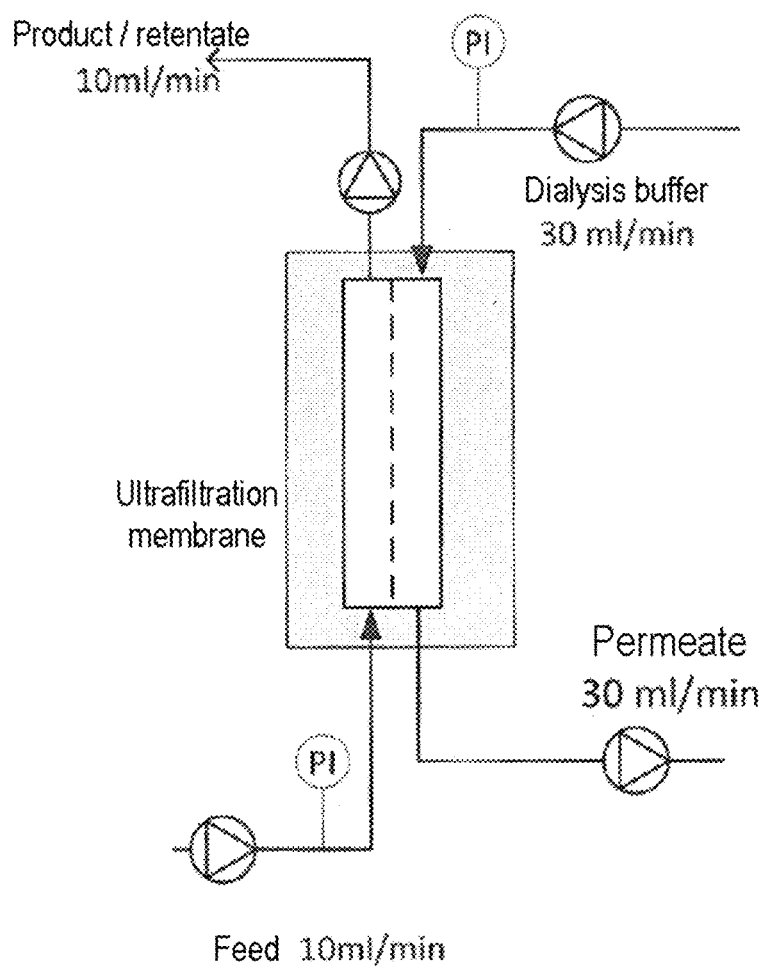
FIGS. 1-3 depict embodiments as shown herein.

Commercially available hollow fibre ultrafiltration modules/capillary ultrafiltration modules are normally used. The molecular weight cut-off (MWCO) of the ultrafiltration membrane here should be selected such that the membrane retains the target product in the hollow fibres/capillaries in such a manner that a yield loss ≤90% preferably ≤30% and particularly preferably ≤10% is not exceeded. At the same time, smaller molecules and ions are not retained by the membrane. Yield loss means the loss of the product permeating through the membrane in comparison to the product in the feed stream, and is usually measured or analysed by measurement of a sample with one of the known methods, such as for example chromatographic methods, ELISA, etc.

It is advantageous that capillary ultrafiltration modules are commercially available steam-sterilized or gamma-sterilized, corresponding to the requirements of the pharmaceutical industry. For example in one test plant haemodialysis modules Revaclear 300 Capillary Dialyzer from Gambro, comprising capillaries of a polymer blend of polyaryl ether sulphones (PAES) and polyvinylpyrrolidone (PVP) with an internal diameter of 190 μm and with a wall thickness of 35 μm were used (http://www.gambro.com/PageFiles/21256/Revaclear%20White%20Paper.pdf?epslanguage=en).

Alternatively a hollow fibre module such as for example the Process Scale Ultrafiltration Hollow Fiber Cartridge (UFP-750-E-55A) from GE Healthcare is also usable.

According to the invention, the feed stream is conveyed in a controlled manner into the hollow fibres/capillaries of the ultrafiltration module and a washing fluid is conveyed in a controlled manner into the jacket side. The retentate is conveyed in a controlled manner out of the hollow fibres/capillaries and passed on into the plant. Surprisingly, it was found that the buffer exchange can be successfully performed without circulation of the product stream. This already occurs with the use of a single ultrafiltration module. It can however be advantageous to connect several ultrafiltration modules in series or parallel. In the method, the washing fluid is pumped either in co-current, cross-current or countercurrent, preferably in cross-current, particularly preferably in countercurrent to the feed stream. Operation in countercurrent, in which the product stream (e.g. the protein solution in buffer A) here flows upwards from below through the hollow fibres/capillaries of the ultrafiltration module while the washing fluid (buffer S) on the jacket side is usually passed downwards from above past the hollow fibres/capillaries, enables higher purity (buffer exchange efficiency) with less washing fluid. Likewise, the product stream can flow downwards from above through the capillaries of the haemodialysis module while the washing fluid on the jacket side is passed upwards from below past the capillaries. Surprisingly it was found that this simple solution enables efficient buffer exchange of the product stream even in continuous operation.

For conveying the product stream (=feed stream) and the washing fluid (=permeate) in each case one pump is used. For the controlled removal of the product stream from the capillaries (=retentates), one further pump or a control valve is used as means for controlled removal of the product stream. Through the use of a pump for controlled removal of the retentate (=retentate pump), control of the removal of the retentate is simplified. Precisely in the use of the sterile disposable technology, this is particularly advantageous at low flow rates, since here there are no adequate flow sensors which reliably measure lower flow rates (≤100 ml/min). Particularly preferably, peristaltic pumps can be used here with the advantage that peristaltic disposable pumps are commercially available, so that sterility and also disposable technology are available.

If only three pumps, i.e. the two pumps for conveying the feed stream (=feed pump) and the permeate (=permeate pump) and the retentate pump, the fourth stream is uncontrolled. Possible malfunctions in one of the three pumps can remain unnoticed. Preferably, therefore, for controlled removal of the washing fluid the pressure ratio between capillary and jacket side (=outer side) is adjusted. This is also usually effected by use of a further pump or a control valve for removal of the washing fluid as a means for controlled removal of the washing fluid. Ultrafiltration units according to the invention comprising a capillary ultrafiltration module are shown by way of example in FIGS. 1 and 2 without being restricted thereto.

The feed stream and the washing fluid flow (=dialysis buffer) are created via pumps. The retentate flow is preferably created via a positive displacement pump such as a peristaltic pump (FIG. 1), or alternatively via a control valve and a flow control (embodiment not shown).

Figure 2:
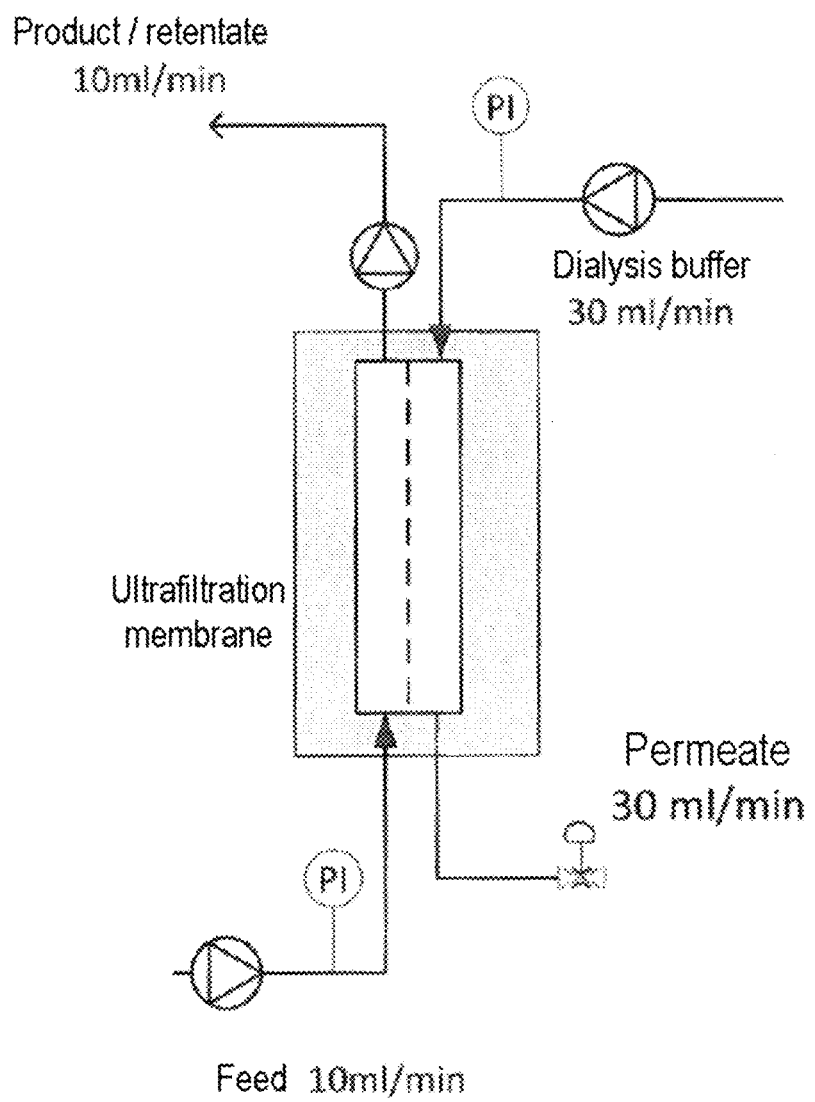

Preferably, the ratio of the pressures of the inlet flows (FIG. 1, feed and dialysis buffer) is regulated in order to avoid a short circuit flow from one membrane side to the other. For this, as shown in FIG. 1, an additional fourth pump in the permeate outlet can be used (FIG. 1) or preferably the permeate outlet is throttled by a valve or hydrostatic pressure (FIG. 2).

In the embodiment with four pumps, three pumps, the two pumps for conveying the feed stream and the washing fluid (=permeate pump) and the retentate pump, preferably run under control, while the pump for controlled removal of the washing fluid (=waste pump) is regulated via a pressure sensor. More precisely, the waste pump is triggered such that the pressure in the haemodialysis module is controlled e.g. to 200 mbar, measured on the permeate side. This pressure-controlled waste pump must then convey precisely the volume flow/flow rate of the feed pump. At lower flow rates, one of the inward conveying pumps, feed or permeate pump, or one of the outward conveying pumps (retentate or waste pump) is defective. In this manner, without flow measurement it is possible to monitor whether all pumps are pumping correctly.

Preferably, a valve or hydrostatic pressure can be used for pressure control of the permeate outlet.

Figure 3:
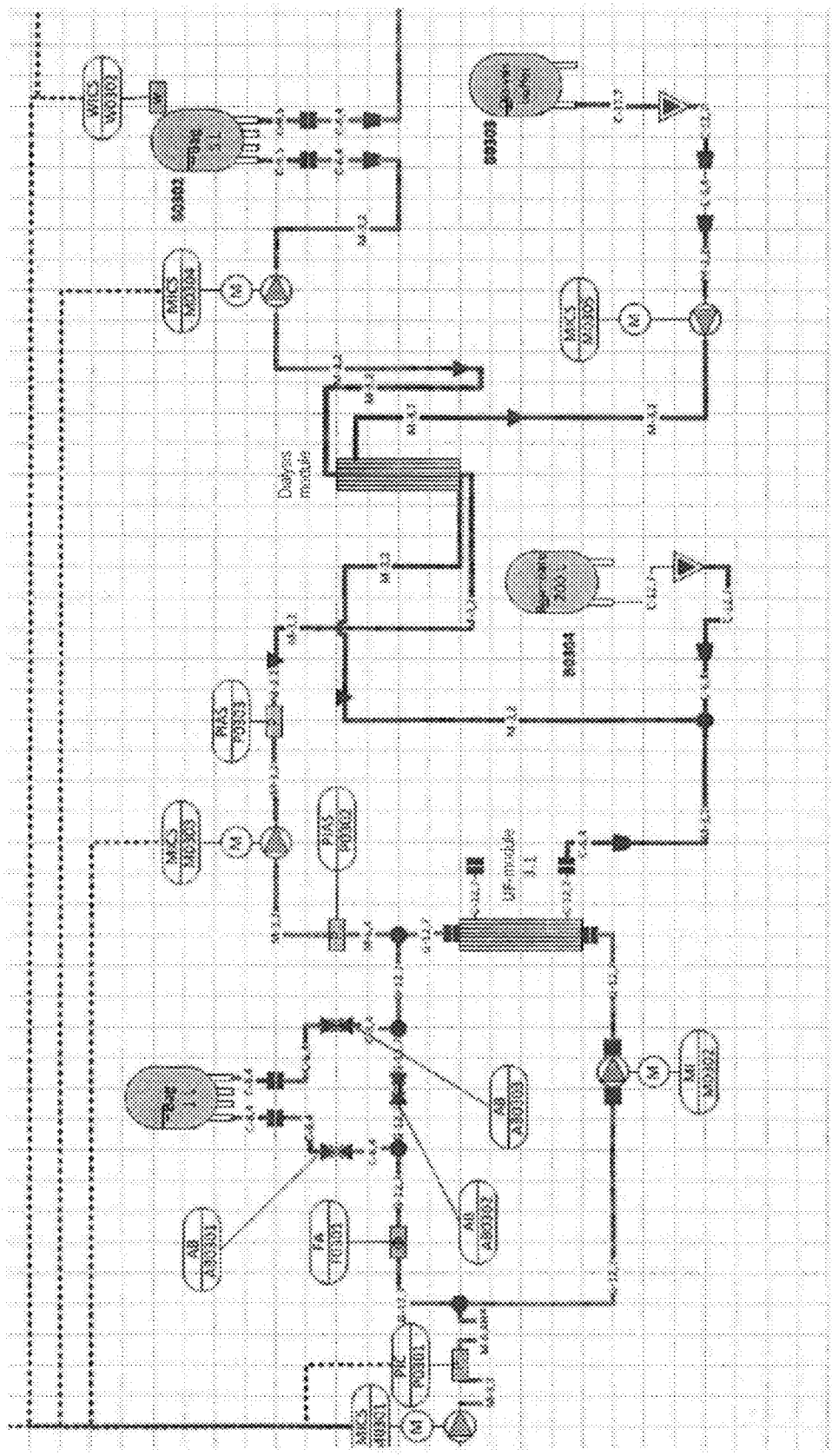

A further embodiment of the ultrafiltration unit is shown diagrammatically in FIG. 3 without being restricted thereto. A pump M0303 conveys a volume flow into one or more haemodialysis modules (DF module). Preferably, one or more haemodialysis modules are connected in series. A pressure sensor P0303 preferably monitors the feed pressure of the ultrafiltration unit. If this rises above the maximal pressure, the stage is shut down. After the ultrafiltration unit, the pump M0304 preferably pumps exactly as fast as M0303 in order to prevent a change in the product concentration in the haemodialysis module and formation of a gel layer on the membrane. The pump M0304 conveys the dialysed retentate into an intermediate bag B0302. The washing fluid is pumped by the pump M0305 at a faster flow rate than M0303 into the permeate side of the haemodialysis modules (=jacket side of the capillary). The flow rate of the pump M0303 here is set sufficiently high for the desired concentrations of buffer in the retentate to be reached. The used washing fluid is collected in bag B0304.

The first subject of the present application is a unit for continuous ultrafiltration of a product stream which contains biopharmaceutical and biological macromolecular products, which comprises at least one capillary ultrafiltration module, characterized in that at least one pump conveys the product stream into the capillaries of the ultrafiltration module, a pump conveys the product stream from the capillaries and at least one further pump passes the washing fluid over the outside of the capillaries, with no measures for circulating the product stream and the washing fluid through the ultrafiltration module.

Preferably, a means for controlled removal of the washing fluid from the ultrafiltration module is used.

A further subject of the application is a method for continuous ultrafiltration of a feed stream, containing biopharmaceutical and biological macromolecular products in the unit according to the invention for continuous ultrafiltration, characterized in that the feed stream is washed with a washing fluid via at least one capillary ultrafiltration membrane of a capillary ultrafiltration module, in that the feed stream is conveyed into the capillary and the washing fluid is passed over the outside of the capillary, in that the feed stream is continuously fed into the ultrafiltration module and the washing fluid is continuously fed in and is continuously removed from the ultrafiltration module, in that the feed stream and the washing fluid are not circulated through the ultrafiltration module.

In order to achieve efficient exchange of small molecules and ions between the membrane sides, the net volume flow across the membranes is as far as possible minimized so that, as in a dialysis method, the transport as far as possible takes place by diffusion. Diffusive transport is in particular achieved when the dilution or concentration of the non-permeating substances takes place with a factor of at most 1 to 5, preferably with a factor of 1 to 2, particularly preferably with a factor of 1.

According to the invention, several ultrafiltration modules can be connected in series or parallel. The number of ultrafiltration modules in series here should be selected such that the overall pressure loss across the ultrafiltration modules does not exceed 1 bar. The number of ultrafiltration modules connected in parallel should be selected such that the feed stream into the capillaries does not exceed the maximal flow rate recommended by the manufacturer; a flow rate of 0.1 to 15% of the recommended flow rate, especially 0.1 to 5% of this flow rate, is preferable.

For example, in the test plant, haemodialysis modules Revaclear 300 Capillary Dialyzer from Gambro were used. In these modules, the feed stream should not exceed 500 ml/min, preferably 75 ml/min, still better 25 ml/min per module. Modules can be connected in series such that the overall pressure difference between the inlet and the outlet of the modules (=pressure loss across the membranes of the capillary ultrafiltration modules) do not exceed the recommended flow rate of 1 bar.

In order to achieve as high as possible depletion of the impurities in the retentate, the ratio of the flow of washing fluid (=dialysate stream) to feed stream is usually selected as high as possible. The exact level of this ratio depends on the minimum depletion required, as well as the diffusion rate of the molecules. At the same time, the dialysate stream in one module should also not exceed the maximum flow recommended by the manufacturer. From an economic point of view also, it is advisable to limit the dialysate stream. For a diafiltration process operated batchwise, it is common practice to set a ratio of washing fluid volume to feed fluid volume of 3-6, sometimes 10. In the method according to the invention, a comparable setting of the ratio of dialysate streams to feed streams of 3-6 can be selected as a first approach and is as a rule adapted experimentally to the properties of the product.

It was surprisingly found that the priming (start-up by washing and deaeration) of the dialysis modules is decisive for the washing quality, since otherwise not all capillaries are fully utilized. Because of the preferably low flow rates, a particular difficulty is to deaerate the dialysis modules on the capillary side and also on the jacket side.

According to the invention, before start-up every dialysis module, both the feed side and also the jacket side, is flushed with a buffer solution with at least 10% to 100%, preferably with 15 to 100% and particularly preferably with 30 to 100% of the blood flow rate recommended by the manufacturer until no more gas bubbles escape from the dialysis module. In this case, it is critical that both the feed side and also the jacket side are bubble-free.

According to the invention, the feed and dialysate streams are regulated such that these flows are clearly defined, i.e. no undesired net flows can occur from the feed space (=capillary interior) into the dialysate space (=capillary exterior/jacket side) or vice versa. For this, the following measures can be taken:

Monitoring of the product stream by offline/online signals UV, conductivity, pH, flow measurement, or offline measurements to determine the product quality, such as HPLC, Elisa etc.

It can be advantageous to apply pressure onto the jacket side (=dialysate space) or feed side (=feed space). For this purpose, a means for controlled removal of the respective fluid, either a pump or a valve, can be used at the relevant outlets.

According to the invention, the unit according to the invention for continuous ultrafiltration is integrated into a production plant in particular in a production plant for continuous or semi-continuous implementation of one or more of the aforesaid production steps.

Hence a further subject of the application is a production plant which comprises at least one unit according to the invention for continuous ultrafiltration of a product stream, which contains containing biopharmaceutical and biological macromolecular products.

Furthermore, in many of the aforesaid production steps for production of biopharmaceutical and biological products, a sequence of dilutions and concentrations of the product stream takes place, which represent a challenge for continuous process operation.

Preferably, the production plant according to the invention includes a unit for concentration of the product stream (also named concentration unit) before or after one of the units for continuous ultrafiltration of a product stream. Preferably, the unit according to the invention for continuous ultrafiltration in the production plant is connected to the outlet pipe of a concentration unit.

According to the invention, as shown in FIG. 3 by way of example, the concentration unit comprises a recirculation loop (=concentration loop), and in the concentration loop one or more membrane modules with a permeate outlet, a pump M0302 for adjusting the circulatory flow in the concentration loop and a deaeration bag (no numbering). In the concentration loop, the product stream is continuously concentrated. A pump M0301 conveys the product stream usually from a holding bag into the concentration loop. As the membrane module, one or more CFF ultrafiltration modules (Cross Flow Filtration) or alternatively ATF (Alternating Tangential Flow) ultrafiltration modules, but preferably one CFF module, are normally used. For example, in the test plant CFF modules RTP UFP-30-C-5S from GE Healthcare Life Science are used.

The flow rate from M0302 is usually set to at least the minimum overflow rate which is stated by the membrane manufacturer. For example, for the module RTP UFP-30-C-5S at least 2 l/min is set.

The pump M0303 conveys the product stream out of the concentration loop. Here the flow rate of the pump M0303 is set in relation to the flow rate of the pump M301. This ratio corresponds to the desired concentration factor. In this case, a pressure is set at the pressure sensor P0301 and P0302, which causes the liquid from the concentration loop to permeate through the membrane, during which however the biological product is as far as possible retained. Usually a membrane is used which retains at least 90%, preferably 90-95%, particularly preferably 95-100% of the biological product. In the design described, a pump is used which can also hold a supply pressure without the liquid flowing through the pump and not through the membrane. A peristaltic pump is preferably used here. As an alternative, a control valve-flowmeter combination through which the permeate flow is adjusted can also be used.

The permeate passing through the membrane of the membrane module is collected through the permeate outlet in the container B0304. The pressure sensor P0301 between the pump M0301 and the concentration loop monitors the pressure before the membrane module and can lead to the shutdown of M0302 if a maximal pressure is exceeded. In this case, the membrane module must be changed. Preferably in this case, the concentration loop is replaced as a whole by a fresh sterilized one. However, in the use of membrane cassettes it is entirely normal to operate cassettes in parallel. The membrane cassettes can be arranged in series or in parallel, preferably in parallel. Usually a pressure sensor P0302 measures the pressure behind the concentration loop, whereby the transmembrane pressure can be determined. Usually a flow sensor F0301 (not shown) measures the volume flow in the concentration loop. In a fixed ratio to the flow rate of M0301, the pump M0303 conveys a volume flow from the concentration loop out into the ultrafiltration unit.

Maintenance of sterility is a further challenge and problem for a (semi)continuous production plant. In the production plant according to the invention, all components are connected together by tubes, in particular disposable tubes. For example, biocompatible tubes Pharmed BPT® (heat-resistant silicone tubes) are used. The other components of the plant are also preferably disposable components; in particular, components selected from the group of disposable reactors, disposable filtration elements, disposable valves, disposable sensors (flow, pH, conductivity, UV, pressure), disposable cell retention systems, disposable tubes, disposable membranes, disposable connectors, disposable chromatography columns, disposable containers and disposable sampling systems are used. Means for conveying liquid, in particular pumps, are also preferably disposable pumps.

For changing the membrane module and/or an ultrafiltration module, the product stream is usually interrupted and an interim bag (holding bag B0301 in FIG. 3) fills for the duration of the change.

Through the use of units for sterile filtration for further reduction of the bioburden, the lifetime of the particular modules can be improved such that an interruption and the capture (=storage) of the product stream in an interim bag for the duration of the change is justifiable.

Alternatively to the concentration loop, one or more Cadence™ Single-Pass Tangential Flow filtration cassettes from Pall Corp can be used as units for concentrating the product stream (U.S. Pat. No. 7,682,511 B2, http://www-.pall.com/main/biopharmaceuticals/product-.page?id=52742).

Through the concentration step, the volume flow is markedly decreased and the product concentration increased.

Example and Test Plant:

To investigate the usability of the solution according to the invention for buffer exchange of a product stream from a fermentation broth, a test plant according to FIG. 3 was constructed as an example. As the tubes of the test plant, Pharmed BPT® tubes with an internal diameter of 3.2 mm were used. In addition to the components of FIG. 3, the test plant included a 10 L container filled with a fermentation broth freed from cells as a test product stream. A first pump (M0301) connected by means of tubes with the container (not shown) firstly conveyed the product stream as shown in FIG. 3 into the concentration unit. As the test molecule, an immunoglobulin G antibody (IgG antibody) was chosen.

The concentration unit comprised a pump M0302 for circulation/flow into the concentration loop, a deaeration bag (no numbering) connected by means of tubes and manual pinch valves AB0301, AB0302 and AB0303 with the concentration loop and a membrane module (UF module 3.1). As the membrane module, by way of example a CFF ultrafiltration module RTP UFP-30-C-5S from GE Healthcare LifeScience was used.

The flow rate of M0302 was set to the minimal overflow speed which is stated by the membrane manufacturer. For example, for the module RTP UFP-30-C-5S at least 2 l/min was set. Before the actual concentration, the concentration loop is firstly deaerated by partly opening AB0301 and AB0303 and AB0302. When the concentration loop is bubble-free, AB0302 is fully opened and AB0301 and AB0303 closed.

The pump M0303 conveyed the product stream out of the concentration loop. At the same time the flow rate of pump M0303 was set in the ratio to the flow rate of pump M0301 which corresponded to the desired concentration factor. At the pressure sensor P0301 and P0302, a pressure was established which caused liquid from the concentration loop to permeate through the membrane, during which however the biological product was as far as possible retained.

The permeate passing through the membrane of the membrane module was collected in the container B0304. The pressure sensor P0301 between the pump M0301 and the concentration loop monitored the pressure before the membrane module and could lead to shutdown of M0302 if a maximal pressure was exceeded. In this case, the membrane module had to be changed. The pressure sensor P0302 measured the pressure behind the concentration loop, whereby the transmembrane pressure could be determined. A flow sensor F0301 (not shown) measured the volume flow in the concentration loop.

The pump M0303 conveyed a volume flow from the concentration unit into the following ultrafiltration unit in a fixed ratio to the flow rate from M0301.

In the test plant, as shown in FIG. 3, the ultrafiltration unit comprised a haemodialysis module (dialysis module) Revaclear 300. Capillary Dialyzer from Gambro containing capillaries of a polymer blend of polyaryl ether sulphone (PAES) and polyvinylpyrrolidone (PVP) with an internal diameter of 190 µm and with a wall thickness of 35 µm used (http://www.gambro.com/PageFiles/21256/Revaclear%20White%20Paper.pdf?epslanguage=en).

Pump M0303 conveyed a volume flow into the haemodialysis module. A pressure sensor P0303 monitored the feed pressure of the ultrafiltration unit.

Before start-up of the haemodialysis module, both the feed side and also the jacket side were washed with a buffer solution (=washing fluid) at 80-100 ml/min blood flow rate, until no more gas bubbles escaped from the module (priming) It was critical here that both the feed side and the jacket side were bubble-free.

For the buffer exchange of the product stream, the feed stream was then set to 3 ml/min per module.

The dialysis buffer (washing fluid) was pumped with the pump M0305 with a flow rate of 3 or 6 ml/min as that from M0303 in countercurrent to the feed stream into the permeate side of the haemodialysis module or modules. The flow rate in M0303 here was set high enough for the desired concentrations of buffers in the product to be reached. The used washing fluid was collected in bag B0304.

The feed and dialysate streams were regulated/controlled such that these flows are clearly defined, i.e. no undesired net flows from the feed space (capillary interior) into the dialysis space (capillary exterior) or vice versa could occur.

For this the following measures were taken:

Monitoring of the product stream by offline/online signals such as UV, conductivity, pH, flow measurement or offline measurements to determine the product quality, such as HPLC or Elisa.

After the ultrafiltration unit, in order to prevent a change in the concentration of the product in the dialysis module and formation of a gel layer on the membrane, the pump M0304, conveyed the concentrated and dialysed product stream at exactly the same speed as M0303 into an interim bag B0302, the filling whereof was monitored with a weighing cell W0302.

Loss of yield and successful buffer exchange of the product stream were checked by determinations of the concentrations of product, glucose and salt.

In a first experiment, the ion exchange was tested with a product stream containing no biological product. Table A shows the measurements of the conductivity of the feed (Cond. feed) and of the retentate (Cond. retent.) with different target flow rates of the respective pumps.

TABLE A

Ion exchange with no biological product

Feed: 0.1 molar acetate pH 7.5 (HCl)/washing fluid: fully deionized water

| Run time Hrs | Cond. feed µS/cm Cond 3 | Cond. retent. µS/cm Cond 4 | Wash in target g/min | Feed in target g/min | Retentate g/min | Permeate g/min |
|---|---|---|---|---|---|---|
| 0.00 | | | | | | |
| 0.25 | 7200 | 3.1 | 2.8 | 2.8 | 3.1 | 3.1 |
| 0.33 | 7200 | 1.5 | 3 | 3 | 3.4 | 3.2 |
| 0.67 | 7200 | 1.5 | 3 | 3 | 3.1 | 3.0 |
| 1.03 | 7200 | 1.5 | 3 | 3 | 3.2 | 3.1 |
| Flow rates increase | | | | | | |
| 0.05 | 7200 | 394 | 20 | 20 | 28.7 | 31.7 |
| 0.17 | 7200 | 1000 | 30 | 30 | 31.3 | 32.3 |
| 0.33 | 7200 | 1193 | 30 | 30 | 31.7 | 32.5 |
| 0.67 | 7200 | 1233 | 30 | 30 | 30.8 | 31.8 |
| 0.90 | 7200 | 1233 | 30 | 30 | 31.3 | 32.1 |

0.1 molar acetate pH 7.5 (HCl)/washing fluid: fully deionized water

| Run time Hrs | Cond. feed µS/cm Cond 3 | Cond. retent. µS/cm Cond 4 | Wash in target g/min | Feed in target g/min | Retentate g/min | Permeate g/min |
|---|---|---|---|---|---|---|
| 0.03 | 10230 | 423 | 30.0 | 15.0 | 33.0 | 66.5 |
| 0.17 | 10230 | 65 | 60.0 | 30.0 | 30.6 | 64.4 |
| 0.50 | 10230 | 52 | 60.0 | 30.0 | 30.9 | 65.2 |
| 0.67 | 10230 | 51 | 60.0 | 30.0 | 30.9 | 66.6 |

TABLE A-continued

Ion exchange with no biological product

| Flow rates increase | | | | | | |
|---|---|---|---|---|---|---|
| 0.03 | 10230 | 10 | 40.0 | 45.0 | 32.0 | 88.5 |
| 0.25 | 10230 | 9 | 80.0 | 25.4 | 31.1 | 89.5 |
| 0.50 | 10230 | 9 | 80.0 | 30.0 | 31.3 | 89.8 |
| 0.67 | 10230 | 9 | 80.0 | 30.0 | 31.0 | 89.7 |

In a further experiment, the ion exchange was tested with a product stream containing IgG antibody (measured by HPLC Prot A).

Table B shows the measurements of the conductivity of the retentate (Cond. retent.) at various target flow rates of the relevant pumps and the concentration of the IgG antibody in the retentate measured by HPLC Prot A.

In the permeate also, the concentration of the IgG in the combined sample at elevated flow rates was determined with the aforesaid method for calculation of the yield loss. According to this, the yield loss in the permeate was 1.4%.

The measurement of the concentration of sodium acetate by ion chromatography demonstrates the successful buffer exchange of the product stream.

TABLE B

Dialysis experiment with antibody
Feed: IgG fermenter broth containing 1136 mg/l antibody IgG and 128 mM NaAc
Washing buffer: 50 mM imidazole/50 mM NaCl pH 7, Cond. 7.6 mS/cm

| Run time hrs | Cond. retent. mS/cm Cond 4 Conductivity mS/cm | Analyses mg/l Prot A | Content mM NaAc | Wash target g/min | Feed target g/min | Retentate g/min | Permeate g/min |
|---|---|---|---|---|---|---|---|
| 0.00 | 0.40 | | | | | | |
| 0.08 | 5.55 | | | 3 | 3 | 3.00 | 3.20 |
| 0.17 | 6.40 | | | 3 | 3 | 3.20 | 3.40 |
| 0.25 | 6.93 | | | 3 | 3 | 3.20 | 3.20 |
| 0.33 | 7.12 | | | 3 | 3 | 3.00 | 3.20 |
| 0.42 | 7.22 | | | 3 | 3 | 3.00 | 1.40 |
| 0.50 | 7.26 | | | 3 | 3 | 3.20 | 5.20 |
| 0.67 | 7.26 | | | 3 | 3 | 3.00 | 3.10 |
| 0.83 | 7.22 | | | 3 | 3 | 3.00 | 3.40 |
| 1.00 | 7.17 | 987.57 | 3.30 | 3 | 3 | 3.00 | 3.20 |
| Wash buffer flow increase | | | | | | | |
| 0.17 | 7.31 | | | 3 | 6 | 3.10 | 6.50 |
| 0.33 | 7.59 | | | 3 | 6 | 3.10 | 6.40 |
| 0.50 | 7.65 | | | 3 | 6 | 3.10 | 6.50 |
| 0.67 | 7.66 | | | 3 | 6 | 3.10 | 6.50 |
| 1.50 | 7.67 | 1067.82 | <0.3 | 3 | 6 | 3.12 | 6.46 |
| Permeate | | 7.71 | | | | | |

The work which led to this application was supported in accordance with the financial aid agreement "Bio.NRW: MoBiDiK-Modular Bioproduction—Disposable and Continuous" in the context of the European Regional Development Fund (ERDF).

The invention claimed is:

1. A method for continuous ultrafiltration of a feed stream containing biopharmaceutical and biological macromolecular products in a unit for continuous ultrafiltration, wherein the feed stream is washed with a washing fluid via at least one capillary ultrafiltration membrane of a capillary ultrafiltration module, wherein the feed stream is conveyed into the capillary and the washing fluid is conveyed over the outside of the capillary, wherein the feed stream and the washing fluid are continuously fed into the ultrafiltration module, and are continuously removed from the ultrafiltration module, wherein the feed stream and the washing fluid is not circulated into the capillary ultrafiltration module and the removal of a product stream comprising a retentate is regulated such that no undesired net flows can pass from the capillary interior to the capillary exterior or vice versa, wherein the capillary ultrafiltration module is bubble free on both a feed side and a jacket side via a priming procedure in which both the feed side and the jacket side are flushed with buffer solution until no more gas bubbles escape from the ultrafiltration module, and wherein both the feed side and the jacket side are flushed by the buffer solution at a flow rate ranging between 10% and 100% of a blood flow rate.

2. The method according to claim 1, wherein in the unit for continuous ultrafiltration, product in the feed stream is at most concentrated by a factor of 2.

3. The method according to claim 1, wherein the washing fluid is passed in cross-current configuration to the feed stream.

4. The method according to claim 1, wherein a plurality of the at least one capillary ultrafiltration modules is connected in series and the maximum pressure drop over membranes of the capillary ultrafiltration modules does not exceed 1 bar.

5. The method according to claim 1, wherein in the unit for continuous ultrafiltration, product in the feed stream is at most diluted by a factor of 2.

6. The method according to claim 1, wherein the washing fluid is passed in countercurrent configuration to the feed stream.

7. The method according to claim 1, wherein a plurality of the at least one capillary ultrafiltration modules are connected in parallel and the maximum pressure drop over membranes of the capillary ultrafiltration modules does not exceed 1 bar.

8. The method according to claim 1 wherein the flow rate ranges between 15% and 100% of the blood flow rate.

9. The method according to claim 1 wherein the flow rate ranges between 30% and 100% of the blood flow rate.

\* \* \* \* \*